US00PP31983P2

(12) United States Plant Patent
Skotak, Jr.

(10) Patent No.: US PP31,983 P2
(45) Date of Patent: Jul. 14, 2020

(54) ***XPORTMEA* PLANT NAMED 'DURALIL'**

(50) Latin Name: ***Aechmea smithiorum* var. *longistipitata* x *Portea alatisepela***
Varietal Denomination: DURALIL

(71) Applicant: Chester Skotak, Jr., Alajuela (CR)

(72) Inventor: Chester Skotak, Jr., Alajuela (CR)

( * ) Notice: Subject to any disclaimer, the term of this patent is extended or adjusted under 35 U.S.C. 154(b) by 0 days.

(21) Appl. No.: 16/501,729

(22) Filed: May 29, 2019

(51) Int. Cl.
*A01H 5/02* (2018.01)
*A01H 6/22* (2018.01)

(52) U.S. Cl.
USPC ..... Plt./370

(58) Field of Classification Search
USPC ..... Plt./263.1, 370
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct x*Portmea* cultivar named 'DURALIL' which is characterized by an elongated compound spike inflorescence, a light pink peduncle and secondary branches, large pink bracts subtending the secondary branches of the inflorescence, secondary conduplicate bracts which envelope each flower bud along the length of the secondary branches, secondary bracts which are vibrant dark red-purple and fading to light pink towards the base, as well as the stability of these characteristics from generation to generation.

3 Drawing Sheets

Latin name of the genus and species: The Latin name of the genus and species of the novel variety disclosed herein is *Aechmea smithiorum* var. *longistipitata* x *Portea alatisepela* which is also known by the nothogenus, x*Portmea.*

Variety denomination: The inventive variety of x*Portmea* disclosed herein has been given the variety denomination 'DURALIL'.

BACKGROUND OF THE INVENTION

Parentage: The x*Portmea* variety 'DURALIL' is the result of a controlled pollination breeding program carried out in 2005 in Alajuela, Costa Rica. The new variety originated as a seedling from the crossing of an *Aechmea smithiorum* var. *longistipitata* plant (unpatented), the seed parent, with an unnamed *Portea alatisepela* plant (unpatented) as the pollen parent. 'DURALIL' was first observed in 2008 and was noted for unique inflorescence.

Asexual Reproduction: Asexual reproduction of the new cultivar 'DURALIL', by way of mericloning, was first initiated in 2016 at a tissue culture laboratory in Evergem, Belgium. Through five subsequent generations, the unique features of this cultivar have proven to be stable and true to type.

SUMMARY OF THE INVENTION

The cultivar 'DURALIL' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'DURALIL'. These characteristics in combination distinguish 'DURALIL' as a new and distinct x*Portmea* cultivar:

1. x*Portmea* 'DURALIL' exhibits an elongated compound spike inflorescence with pink peduncles and secondary branches; and
2. x*Portmea* 'DURALIL' exhibits an inflorescence with large, primary bracts subtending the secondary branches of the compound spikes; and
3. x*Portmea* 'DURALIL' exhibits secondary conduplicate bracts which envelope each flower bud along the length of the secondary branches; and
4. x*Portmea* 'DURALIL' exhibits secondary bracts which are vibrant dark red-purple and fading to light pink towards the base.

BOTANICAL DESCRIPTION OF THE PLANT

Figure 1:
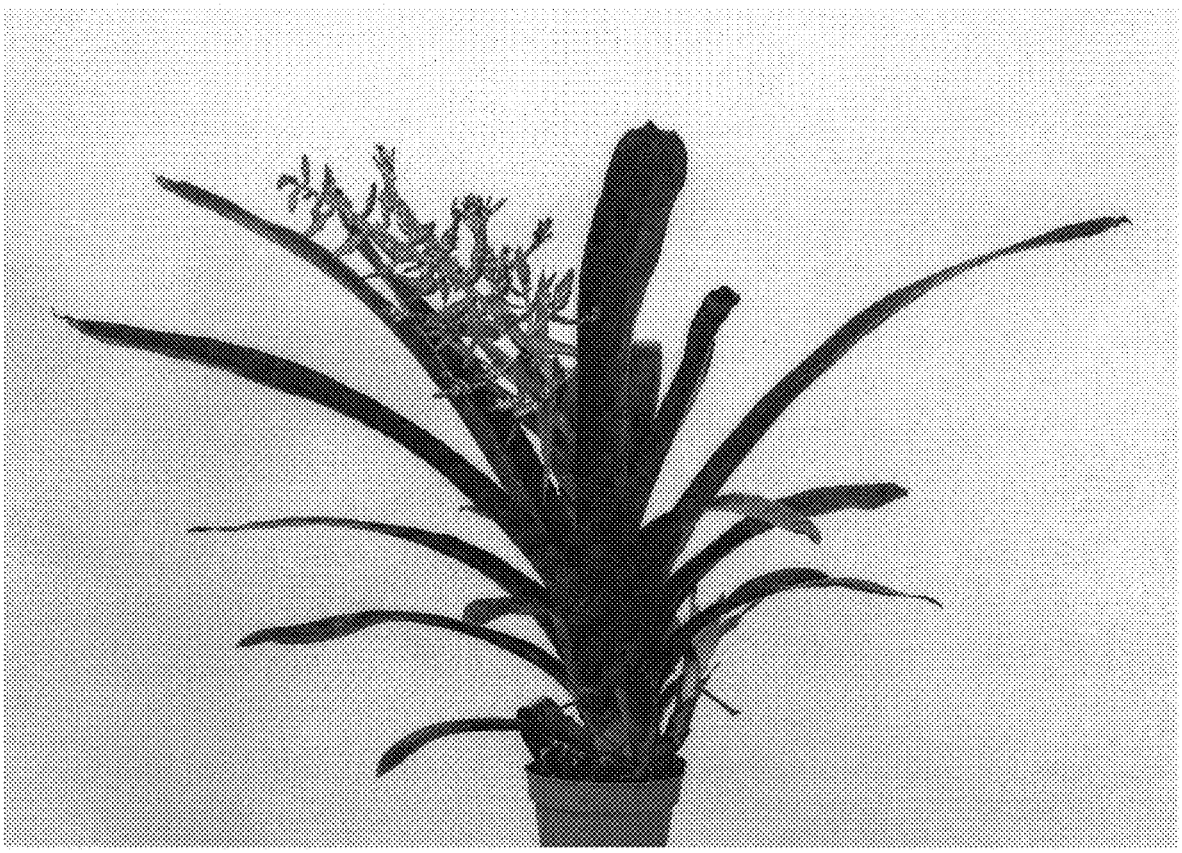
FIG. 1 illustrates, as nearly true as it is reasonably possible to make the same in color photographs of this type, an exemplary plant of 'DURALIL' grown in a commercial greenhouse in Evergem, Belgium. This plant is approximately 18 months old from the time of mericloning, shown planted in a 15 cm nursery container.
Figure 2:
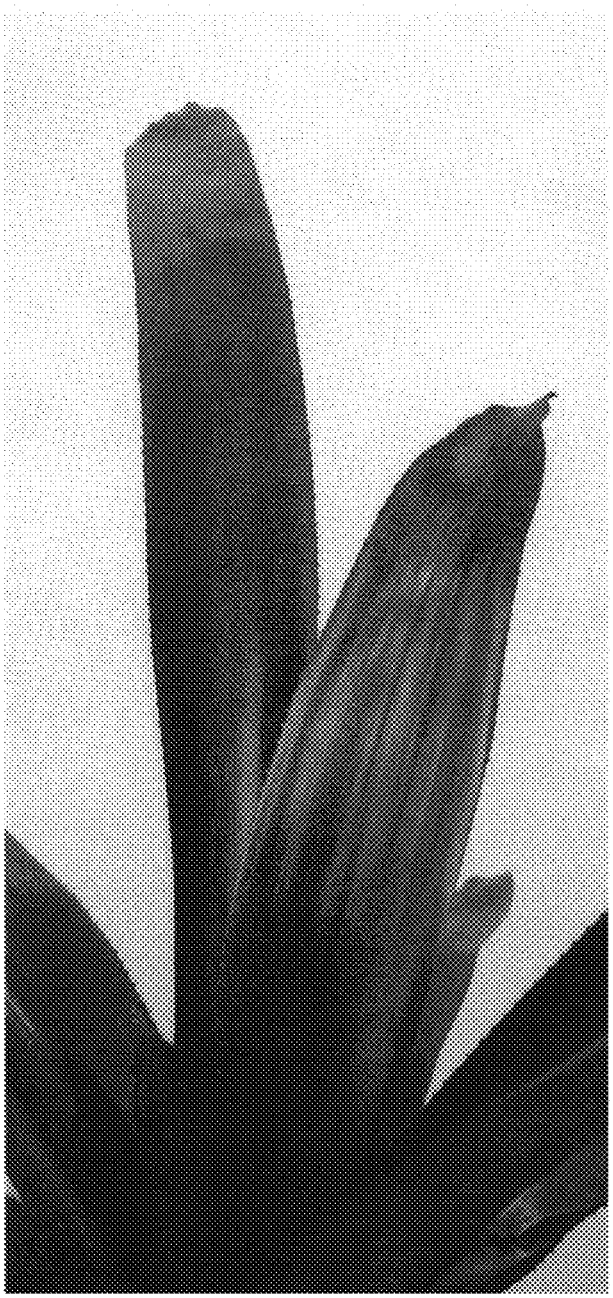
FIG. 2 illustrates, as nearly true as it is reasonably possible to make the same in color photographs of this type, the typical foliage of 'DURALIL'.
Figure 3:
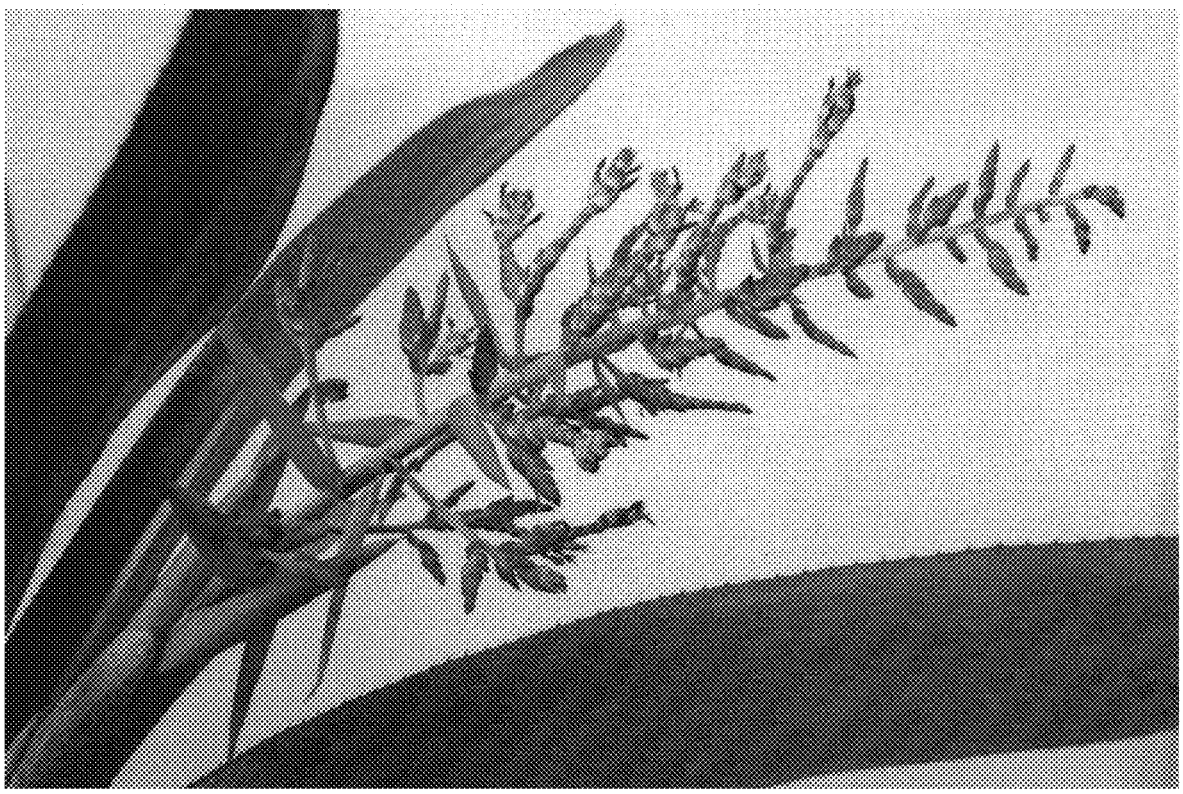
FIG. 3 illustrates, as nearly true as it is reasonably possible to make the same in color photographs of this type, the typical inflorescence of 'DURALIL'.

The following observations and measurements made in April of 2017 describe averages from a sample set of six specimens of 18 month-old 'DURALIL' plants grown in 15 cm nursery pots at a greenhouse in Evergem, Belgium. Plants were produced using conventional greenhouse production protocols for x*Portmea* which consisted of regular overhead irrigation and fertigation applications. No pest or disease control measures were utilized in production. Plants were grown under shade (approximately 12,000 lux maximum) and no photoperiodic treatments or artificial light was given to the plants.

Those skilled in the art will appreciate that certain characteristics will vary with older or, conversely, with younger plants. 'DURALIL' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'DURALIL' and comparisons with the parents and most similar commercial variety are provided below.

Plant description:

*Growth habit*.—Perennial; upright monopodial basal rosette with inflorescences growing from the center of the rosette; a terminal inflorescence is carried above the leaf plane.

*Average height from base to top of foliar plane*.—61.2 cm.

*Average height from base to top of floral plane*.—66.0 cm.

*Plant spread*.—Average of 107.3 cm.

*Growth rate*.—Moderately fast to fast rate of growth.

*Plant vigor*.—Moderately vigorous to vigorous.

*Propagation type*.—Mericloning.

*Time to initiate roots*.—About 14 days at approximately 22 degrees Celsius.

*Time to produce a marketable plant*.—Approximately 18 months.

*Disease and pest resistance or susceptibility*.—Neither resistance nor susceptibility to typical x*Portmea* pests and diseases has been observed.

*Environmental tolerances*.—Adapt to, at least, USDA Zones 10 and 12 and temperatures as high as 40 degrees Celsius; high tolerance to rain; high tolerance to wind.

Root system:

*General*.—Moderately dense rooting; roots are strong.

*Dimensions, mature roots*.—16.5 cm long with a diameter of 0.1 cm, on average.

*Texture*.—Fibrous, non-fleshy.

*Color*.—Brown, nearest RHS N200B.

Stem:

*Branching habit*.—Monopodial; no lateral branches present.

*Number of primary stems per plant*.—None; leaves form a basal rosette.

*Number of secondary branches per plant*.—None.

Foliage:

*Arrangement*.—Rosulate.

*Division*.—Simple.

*Dimensions*.—69.2 cm long, including the leaf sheath, and 7.8 cm wide.

*Aspect*.—Moderately concave.

*Attitude*.—Arching, with the proximal portion has an upward and outward attitude, while the distal portion of the leaf is moderately curved downward.

*Shape of blade*.—Ligulate.

*Apex*.—Bluntly acute.

*Base*.—Sheathing.

*Sheath*.—Dimensions — 13.1 cm long and 10.0 cm wide, on average. Texture and luster, upper and lower surfaces — Smooth, glabrous, and matte. Color — Upper surface — Nearest to in between yellow-green and greyed-green, RHS 151D and 195B. Lower surface — Yellow-green, nearest to RHS 152D.

*Margin*.—Sharply serrate.

*Pubescence, texture and luster of adaxial surface*.—Glabrous, smooth, and moderately glossy.

*Pubescence, texture and luster of abaxial surface*.—Glabrous, smooth, and slightly glossy.

*Color*.—Juvenile foliage, adaxial surface — Nearest to in between green and yellow-green, RHS 143B and 144A. Serrated teeth along the margin are greyed-orange, nearest to a mixture of RHS 166A, 166B and 166C. Juvenile foliage, abaxial surface — Nearest to in between green and yellow-green, RHS 143A and 144A. Serrated teeth along the margin are greyed-orange, nearest to a mixture of RHS 166A, 166B and 166C. Mature foliage, adaxial surface — Green, nearest to in between RHS NN137B and 143A. Mature foliage, abaxial surface — Green, nearest to RHS 143A.

*Venation*.—Pattern — Parallel. Color, adaxial surface — Green, nearest to in between RHS NN137B and 143A. Color, abaxial surface — Green, nearest to RHS 143A.

*Petiole*.—No petioles present, leaves are sessile.

Inflorescence:

*Inflorescence arrangement*.—Terminal compound spike.

*Natural flowering season*.—Spring into autumn in Evergem, Belgium.

*Flowering habit*.—Moderately floriferous.

*Time to flower*—10 weeks after flowering.

*Flowers per inflorescence*.—Approximately 300 unopened buds and 50 open flower.

*Height*.—46.7 cm.

*Diameter*.—24.7 cm.

*Attitude*.—Near vertical.

*Peduncle*.—Dimensions — Approximately 81.5 cm long and 0.8 cm in diameter. Strength — Strong. Texture — Densely covered with stellate pubescence which is colored white, RHS NN155A. Color — Red, nearest to a mixture of RHS 54A and 54B.

Bud:

*Shape*.—Ovate; flattened.

*Length*.—Average of 0.7 cm.

*Diameter*.—0.4 cm at the widest point, and 0.3 cm at the narrowest point.

*Pubescence, texture and luster*.—Glabrous, smooth and glossy.

*Color*.—Violet-blue, RHS 91B, and moderately covered with small dots which are a darker shade of violet-blue, RHS 90B; the base of the bud is yellow-green, nearest to a mixture of RHS 145B, 145C and 145D.

Flower:

*Flower type*.—Rotate, with a single whorl of free petals.

*Attitude*.—Flowers are outward to upward facing.

*Attachment*.—Sessile.

*Diameter.*—0.7 cm.

*Depth.*—2.0 cm.

*Fragrance.*—Not fragrant.

*Lastingness.*—Approximately 3 weeks.

*Persistent.*—Persistent.

*Petals.*—Quantity of petals — 3. Connation — Petals are free. Arrangement — Rotate. Length — Approximately 1.8 cm. Width — Approximately 0.2 cm. Shape — Oblanceolate. Apex — Bluntly acute. Base — Narrowly cuneate. Margin — Entire; moderate undulation. Pubescence, texture and luster of upper surface — Glabrous, smooth, and matte. Pubescence, texture and luster of lower surface — Glabrous, smooth, and matte. Color when opening, upper surface — Brown, RHS N200A, and margined greyed-brown, RHS 199D. Color when opening, lower surface — Brown, RHS N200A, and margined greyed-brown, RHS 199D. Color when fully opened, upper surface — Greyed-brown, nearest to a combination of RHS 199A and 199B. Color when fully opened, lower surface — Brown, RHS N200A. Fading, upper surface — Not fading. Fading, lower surface — Not fading. Venation color, fully opened, upper surface — Greyed-brown, nearest to a combination of RHS 199A and 199B. Venation color, fully opened, lower surface — Brown, RHS N200A.

*Spurs.*—None.

*Calyx.*—Shape — Rotate. Length — 1.3 cm. Width — Calyx is flatted; 0.7 cm at the widest point and 0.6 cm at the narrowest. Sepals — Arrangement — Rotate; single whorl. Connation — Aposepalous. Quantity — 3. Length — 1.0 cm. Width — 0.2 cm. Shape — Narrow obovate. Apex — Bluntly acute. Base — Cuneate. Margin — Entire. Texture and luster, inner surface — Smooth, glabrous, and glossy. Texture and luster, outer surface — Smooth, glabrous, and glossy. Color when opening, inner surface — Violet-blue, RHS 91A. Color when opening, outer surface — Violet-blue, RHS 91A. Color when fully opened, inner surface — Violet-blue, RHS 91A. Color when fully opened, lower surface — Violet-blue, RHS 91A.

*Pedicels.*—Flowers are sessile.

Bracts:

*General description.*—Large, primary bracts subtend the secondary branches of the compound spikes, with secondary conduplicate bracts enveloping each flower bud along the length of the secondary branches. Large, primary bracts — Shape — Lanceolate. Length — 5.9 cm. Width — 2.5 cm. Apex — Narrowly acuminate. Base — Bracts are sessile. Margins — Entire; not undulated to very lightly undulated. Color, inner surface — Red-purple, RHS 72D. Color, outer surface — Nearest to a combination of red-purple, RHS 72D, and yellow, RHS 7B. Secondary conduplicate bracts — Shape — Lanceolate; conduplicate. Length — 1.5 cm. Width — 0.65 cm. Apex — Acute. Base — Broad Cuneate. Margins — Entire; not undulated. Color — Light red-purple towards the base, nearest to RHS 72D, and becoming darker red-purple towards the apex, nearest to RHS 71B.

Reproductive organs:

*Androecium.*—General — Stamens reduced to staminodes. Staminode quantity — 6. Anther — Shape — Narrow oblong. Dimensions — 0.4 cm long and 0.75 cm wide. Color — Greyed-yellow, RHS 160D. Filament — Dimensions — 1.8 cm long and 0.2 cm wide. Color — Brown, RHS N200A, and margined greyed-brown, RHS 199D. Pollen — Amount of pollen — None present. Pollen color — None present.

*Gynoecium.*—Pistil quantity — One. Pistil length — 1.7 cm. Stigma — Shape — Club-shaped. Diameter — 0.1 cm. Color — Greyed-brown, RHS N199D. Style — Length — 1.55 cm. Color — Greyed-brown, RHS N199A, and fading to a lighter shade of greyed-brown, RHS N199D. Ovary — Color — Yellow-green, RHS 145D.

Seed and fruit: Not observed.

COMPARISONS WITH THE PARENT PLANTS

Plants of the new cultivar 'DURALILI' differ from the unnamed *Aechmea smithiorum* var. *longistipitata* seed parent (not patented), by the characteristics described in Table 1.

TABLE 1

| Characteristic | DURALIL' | Seed parent. |
|---|---|---|
| General coloration of the peduncle and secondary branches of the inflorescences. | Pink. | Light green. |
| General coloration of the secondary bracts. | Vibrant, dark red-purple and fading to light pink at the base. | Pale pink. |
| Size of the secondary bracts. | Larger than those of the seed parent. | Smaller than those of 'DURALIL'. |

Plants of the new cultivar 'DURALIL' differ from the unnamed *Portea alatisepela* pollen parent (not patented), by the characteristics described in Table 2.

TABLE 2

| Characteristic | 'DURALIL' | Pollen parent. |
|---|---|---|
| General coloration of the mature foliage. | Lighter green than the pollen parent. | Darker green than 'DURALIL'. |
| General coloration of the peduncle and secondary branches of the inflorescences. | Pink. | Pink and suffused with red. |
| General coloration of the secondary bracts. | Vibrant, dark red-purple and fading to light pink at the base. | Pink and suffused with red. |
| Size of the secondary bracts. | Longer than those of the pollen parent. | Shorter than those of 'DURALIL'. |

COMPARISON WITH THE MOST SIMILAR COMMERCIAL CULTIVAR KNOWN TO THE INVENTOR

'DURALIL' is similar to the commercial variety *Aechmea* x 'Del Mar' (U.S. Pat. No. 13,421) in many horticultural characteristics. However, 'DURALIL' differs from 'Del Mar' in the following characteristics described in Table 3.

TABLE 3

| Characteristic | 'DURALIL' | 'Del Mar' |
|---|---|---|
| Foliage size. | Longer than 'Del Mar'. | Shorter than 'DURALIL'. |
| General coloration of the mature foliage. | Lighter green than the 'Del Mar'. | Darker green than 'DURALIL'. |
| Foliage attitude. | More upright than 'Del Mar'. | Less upright than DURALIL'. |
| Inflorescence size. | More elongated than the inflorescence of the seed parent. | More compact than the inflorescence of 'DURALIL'. |
| Size of the secondary bracts. | Larger than those of the 'Del Mar'. | Smaller than those of 'DURALIL'. |

TABLE 3-continued

| Characteristic | 'DURALIL' | 'Del Mar' |
|---|---|---|
| General coloration of the secondary bracts. | Vibrant, dark red-purple and fading to light pink at the base. | Less vibrant red-purple. |

That which is claimed is:

1. A new and distinct variety of x*Portmea* plant named 'DURALIL', substantially as described and illustrated herein.

* * * * *